US012562241B2

(12) United States Patent
Shi et al.

(10) Patent No.: US 12,562,241 B2
(45) Date of Patent: Feb. 24, 2026

(54) SYSTEM AND METHOD FOR DETECTING ISSUES IN CLINICAL STUDY SITE AND SUBJECT COMPLIANCE

(71) Applicant: Samsung Electronics Co., Ltd., Suwon-si (KR)

(72) Inventors: Yunzhou Shi, San Bruno, CA (US); Yi Yang, Pleasanton, CA (US); Matthew Corbin Wiggins, San Jose, CA (US); Wu Guan, San Jose, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 256 days.

(21) Appl. No.: 17/745,489

(22) Filed: May 16, 2022

(65) Prior Publication Data

US 2022/0375550 A1     Nov. 24, 2022

Related U.S. Application Data

(60) Provisional application No. 63/191,907, filed on May 21, 2021.

(51) Int. Cl.
*G16H 10/20*      (2018.01)
*G16H 20/00*      (2018.01)
*G16H 50/20*      (2018.01)
*G16H 50/70*      (2018.01)

(52) U.S. Cl.
CPC ............ *G16H 10/20* (2018.01); *G16H 20/00* (2018.01); *G16H 50/20* (2018.01); *G16H 50/70* (2018.01)

(58) Field of Classification Search
CPC ........ G16H 10/20; G16H 20/00; G16H 50/20; G16H 50/70; G16H 10/60
See application file for complete search history.

(56) References Cited

U.S. PATENT DOCUMENTS

| | | | |
|---|---|---|---|
| 10,492,725 | B2 | 12/2019 | Abreu Oramas |
| 10,628,553 | B1 | 4/2020 | Murrish et al. |
| 10,810,223 | B2 | 10/2020 | Sundararaman et al. |
| 10,839,951 | B2 | 11/2020 | Sysko et al. |
| 10,945,680 | B2 | 3/2021 | Frieder et al. |
| 2012/0165975 | A1 | 6/2012 | Yi et al. |
| 2013/0268287 | A1 | 10/2013 | Hufford et al. |

(Continued)

OTHER PUBLICATIONS

Kolodziej, et al. "High-Performance Modelling and Simulation for Big Data Applications Selected Results of the COST Action IC1406 cHiPSet", State-of-the-Art Survey, LNCS11400, COST European Cooperation in Science & Technology, Springer Nature Switzerland AG, Cham, Switzerland, 2019, 364 pgs.

*Primary Examiner* — Chinyere Mpamugo

(57) ABSTRACT

A method includes, for each user of a group of users participating in a first clinical study: collecting a plurality of data associated with the user, wherein the plurality of data includes data received from a group of devices used by the user over a duration during the first clinical study; determining a state related to the user based on the plurality of data, wherein the state indicates operating conditions of the group of devices used by the user; determining an event alignment status by aligning events logged by the group of devices based on the state related to the user; and determining an individual compliance score for the user based on the event alignment status. The method also includes providing a recommended duration of the first clinical study based on the individual compliance scores of the group of users.

21 Claims, 5 Drawing Sheets

(56) References Cited

U.S. PATENT DOCUMENTS

| 2020/0175028 A1 | 6/2020 | Kozlowski et al. |
| 2020/0243168 A1 | 7/2020 | Clark et al. |
| 2020/0410614 A1 | 12/2020 | Bonageri et al. |

SYSTEM AND METHOD FOR DETECTING ISSUES IN CLINICAL STUDY SITE AND SUBJECT COMPLIANCE

CROSS-REFERENCE TO RELATED APPLICATION AND PRIORITY CLAIM

This application claims priority under 35 U.S.C. § 119(e) to U.S. Provisional Patent Application No. 63/191,907 filed on May 21, 2021, which is hereby incorporated by reference in its entirety.

TECHNICAL FIELD

This disclosure relates generally to health monitoring systems and methods. More specifically, this disclosure relates to a system and method for detecting issues in clinical study site and subject compliance.

BACKGROUND

Clinical studies are essential to determine safety and efficacy of a medical device or drug. The success rate of clinical studies, however, is not always satisfactory. A 2019 review of average success rates of clinical studies at different phases and diseases over the years 2005-2015 found a success range of 5-14%. To achieve a successful study, besides the performance of the medical device or drug, other important considerations are patient compliance and study yield.

SUMMARY

This disclosure provides a system and method for detecting issues in clinical study site and subject compliance.

In a first embodiment, a method includes, for each user of a group of users participating in a first clinical study: collecting a plurality of data associated with the user, wherein the plurality of data includes data received from a group of devices used by the user over a duration during the first clinical study; determining a state related to the user based on the plurality of data, wherein the state indicates operating conditions of the group of devices used by the user; determining an event alignment status by aligning events logged by the group of devices based on the state related to the user; and determining an individual compliance score for the user based on the event alignment status. The method also includes providing a recommended duration of the first clinical study based on the individual compliance scores of the group of users.

In a second embodiment, an electronic device includes at least one memory configured to store instructions. The electronic device also includes a processor configured when executing the instructions to, for each user of a group of users participating in a first clinical study: collect a plurality of data associated with the user, wherein the plurality of data includes data received from a group of devices used by the user over a duration during the first clinical study; determine a state related to the user based on the plurality of data, wherein the state indicates operating conditions of the group of devices used by the user; determine an event alignment status by aligning events logged by the group of devices based on the state related to the user; and determine an individual compliance score for the user based on the event alignment status. The processor is also configured when executing the instructions to provide a recommended duration of the first clinical study based on the individual compliance scores of the group of users.

In a third embodiment, a non-transitory computer readable medium contains computer readable program code that, when executed, causes at least one processor of an electronic device to, for each user of a group of users participating in a first clinical study: collect a plurality of data associated with the user, wherein the plurality of data includes data received from a group of devices used by the user over a duration during the first clinical study; determine a state related to the user based on the plurality of data, wherein the state indicates operating conditions of the group of devices used by the user; determine an event alignment status by aligning events logged by the group of devices based on the state related to the user; and determine an individual compliance score for the user based on the event alignment status. The computer readable program code, when executed, also causes the at least one processor to provide a recommended duration of the first clinical study based on the individual compliance scores of the group of users.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

As used here, terms and phrases such as "have," "may have," "include," or "may include" a feature (like a number, function, operation, or component such as a part) indicate the existence of the feature and do not exclude the existence of other features. Also, as used here, the phrases "A or B," "at least one of A and/or B," or "one or more of A and/or B" may include all possible combinations of A and B. For example, "A or B," "at least one of A and B," and "at least one of A or B" may indicate all of (1) including at least one A, (2) including at least one B, or (3) including at least one A and at least one B.

As used here, the terms "first" and "second" may modify various components regardless of importance and do not limit the components. These terms are only used to distinguish one component from another. For example, a first user device and a second user device may indicate different user devices from each other, regardless of the order or importance of the devices. A first component may be denoted a second component and vice versa without departing from the scope of this disclosure.

It will be understood that, when an element (such as a first element) is referred to as being (operatively or communicatively) "coupled with/to" or "connected with/to" another element (such as a second element), it can be coupled or connected with/to the other element directly or via a third element. In contrast, it will be understood that, when an element (such as a first element) is referred to as being "directly coupled with/to" or "directly connected with/to" another element (such as a second element), no other element (such as a third element) intervenes between the element and the other element.

As used here, the phrase "configured (or set) to" may be interchangeably used with the phrases "suitable for," "having the capacity to," "designed to," "adapted to," "made to," or "capable of" depending on the circumstances. The phrase "configured (or set) to" does not essentially mean "specifically designed in hardware to." Rather, the phrase "configured to" may mean that a device can perform an operation together with another device or parts. For example, the phrase "processor configured (or set) to perform A, B, and C" may mean a generic-purpose processor (such as a CPU or application processor) that may perform the operations by executing one or more software programs stored in a memory device or a dedicated processor (such as an embedded processor) for performing the operations.

The terms and phrases as used here are provided merely to describe some embodiments of this disclosure but not to limit the scope of other embodiments of this disclosure. It is to be understood that the singular forms "a," "an," and "the" include plural references unless the context clearly dictates otherwise. All terms and phrases, including technical and scientific terms and phrases, used here have the same meanings as commonly understood by one of ordinary skill in the art to which the embodiments of this disclosure belong. It will be further understood that terms and phrases, such as those defined in commonly-used dictionaries, should be interpreted as having a meaning that is consistent with their meaning in the context of the relevant art and will not be interpreted in an idealized or overly formal sense unless expressly so defined here. In some cases, the terms and phrases defined here may be interpreted to exclude embodiments of this disclosure.

Examples of an "electronic device" according to embodiments of this disclosure may include at least one of a smart phone, a tablet personal computer (PC), a mobile phone, a video phone, an e-book reader, a desktop PC, a laptop computer, a netbook computer, a workstation, a personal digital assistant (PDA), a portable multimedia player (PMP), an MP3 player, a mobile medical device, a camera, or a wearable device (such as smart glasses, a head-mounted device (HMD), electronic clothes, an electronic bracelet, an electronic necklace, an electronic accessory, an electronic tattoo, a smart mirror, or a smart watch). Other examples of an electronic device include a smart home appliance.

Examples of the smart home appliance may include at least one of a television, a digital video disc (DVD) player, an audio player, a refrigerator, an air conditioner, a cleaner, an oven, a microwave oven, a washer, a drier, an air cleaner, a set-top box, a home automation control panel, a security control panel, a TV box (such SAMSUNG HOMESYNC, APPLETV, or GOOGLE TV), a gaming console (such as an XBOX, PLAYSTATION, or NINTENDO), an electronic dictionary, an electronic key, a camcorder, or an electronic picture frame. Still other examples of an electronic device include at least one of various medical devices (such as diverse portable medical measuring devices (like a blood sugar measuring device, a heartbeat measuring device, or a body temperature measuring device), a magnetic resource angiography (MRA) device, a magnetic resource imaging (MRI) device, a computed tomography (CT) device, an imaging device, or an ultrasonic device), a navigation device, a global positioning system (GPS) receiver, an event data recorder (EDR), a flight data recorder (FDR), an automotive infotainment device, a sailing electronic device (such as a sailing navigation device or a gyro compass), avionics, security devices, vehicular head units, industrial or home robots, automatic teller machines (ATMs), point of sales (POS) devices, or Internet of Things (IoT) devices (such as a bulb, various sensors, electric or gas meter, sprinkler, fire alarm, thermostat, street light, toaster, fitness equipment, hot water tank, heater, or boiler). Other examples of an electronic device include at least one part of a piece of furniture or building/structure, an electronic board, an electronic signature receiving device, a projector, or various measurement devices (such as devices for measuring water, electricity, gas, or electromagnetic waves). Note that, according to embodiments of this disclosure, an electronic device may be one or a combination of the above-listed devices. According to some embodiments of this disclosure, the electronic device may be a flexible electronic device. The electronic device disclosed here is not limited to the above-listed devices and may include new electronic devices depending on the development of technology.

In the following description, electronic devices are described with reference to the accompanying drawings, according to embodiments of this disclosure. As used here, the term "user" may denote a human or another device (such as an artificial intelligent electronic device) using the electronic device.

Definitions for other certain words and phrases may be provided throughout this patent document. Those of ordinary skill in the art should understand that in many if not most instances, such definitions apply to prior as well as future uses of such defined words and phrases.

None of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle. Use of any other term, including without limitation "mechanism," "module," "device," "unit," "component," "element," "member," "apparatus," "machine," "system," "processor," or "controller," within a claim is understood by the Applicant to refer to structures known to those skilled in the relevant art and is not intended to invoke 35 U.S.C. § 112(f).

BRIEF DESCRIPTION OF THE DRAWINGS

For a more complete understanding of this disclosure and its advantages, reference is now made to the following description, taken in conjunction with the accompanying drawings, in which.

DETAILED DESCRIPTION

Figure 1:
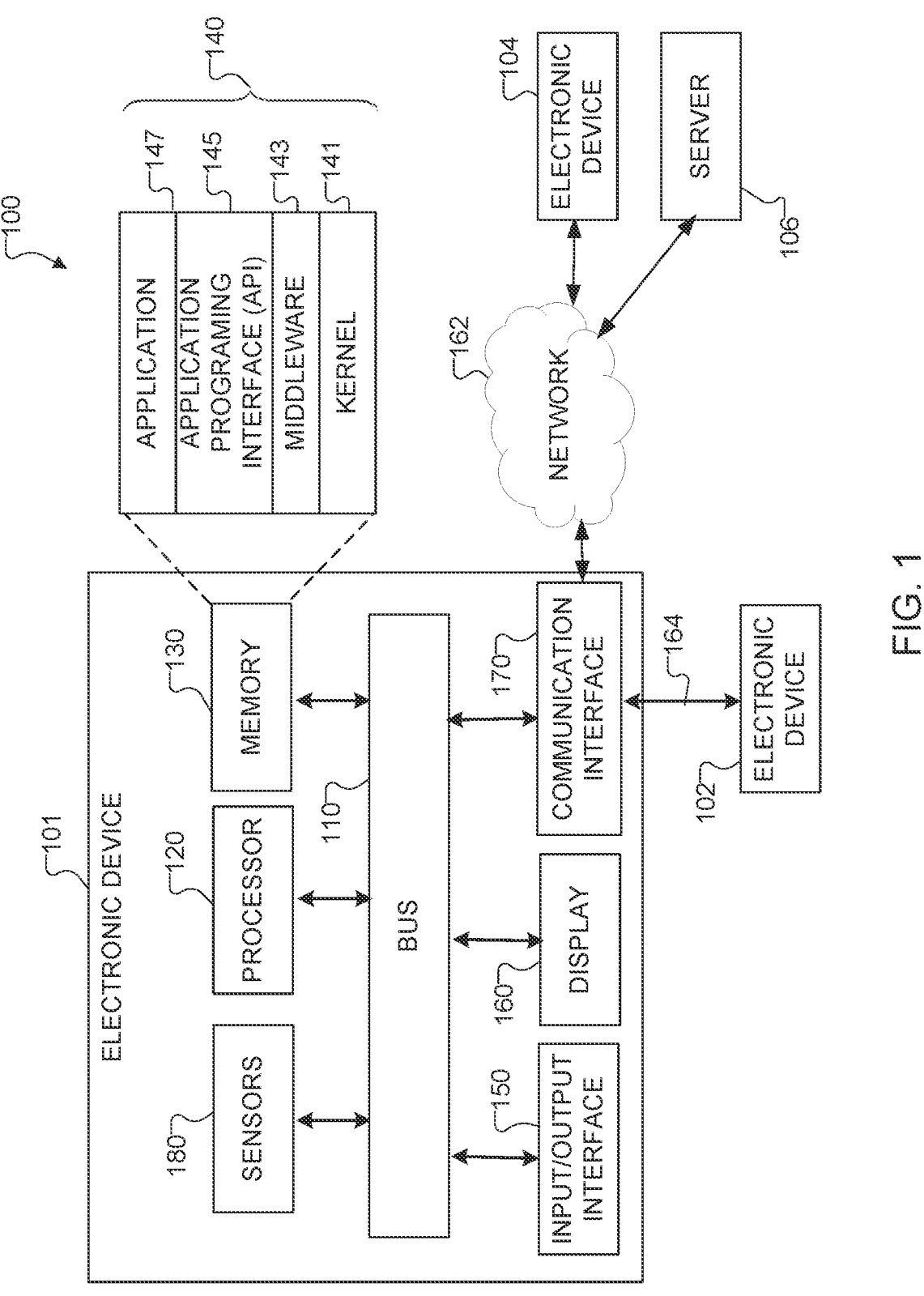
FIG. 1 illustrates an example network configuration according to an embodiment.

The figures discussed below and the various embodiments used to describe the principles of this disclosure in this patent document are by way of illustration only and should not be construed in any way to limit the scope of the disclosure. Those skilled in the art will understand that the principles of this disclosure can be implemented in any suitably arranged system.

As discussed above, clinical studies are essential to determine safety and efficacy of a medical device or drug. The success rate of clinical studies, however, is not always satisfactory. A 2019 review of average success rates of clinical studies at different phases and diseases over the years 2005-2015 found a success range of 5-14%.

Compliance with procedures and treatment can be an important determinant of the outcome of clinical studies. However, widely used methods are inadequate for measuring compliance. For example, if a study site staff deviates from clinical study protocol and misses procedures in a clinical study, study data could be forfeited. As another example, if a subject does not comply with the treatment plan or measurement procedure, the subject's data could bias the study result. The practical issue is that both study site staff and subjects are human beings who are subject to errors. Manual detection of all compliance issues is often difficult or impossible and not scalable. For instance, in multi-site global studies, there are too many subjects to review. Clinical studies often involve hundreds of steps per subject, thus a manual check for all the steps is time consuming and not feasible. Due to the complexity of medical issues, multifaceted data, and de-centralized data locations, tracing all the relevant clues is difficult or impossible. Therefore, traditionally, only major compliance issues are documented, real time correction is not performed, and the impact of compliance issues to clinical study result is often underestimated. Similarly, the site performance evaluation can be inaccurate as not all compliance issues are documented.

To address these and other issues, embodiments of this disclosure provide systems and methods for detecting issues in clinical study site and subject compliance. The disclosed embodiments enable detection of compliance issues using multifaceted data in real-time. The disclosed embodiments use data generated from a group of devices (e.g., mobile devices, wearable devices, medical devices, and the like) during a clinical study. The data is evaluated and processed in real time to determine compliance issues. The compliance detection process is based on the evaluation of the interoperability of data generated from the applications running on the different devices. In some embodiments, the data not only includes raw signals under test (e.g., ECG, blood pressure, $SpO_2$, heart rate, and the like), but also system event details captured during the entire journey of the clinical study.

The disclosed embodiments can be used for simultaneously managing large scale clinical studies (e.g., multi-center, multi-study) with minimal human interventions. In addition, the disclosed embodiments can be used for healthcare services such as monitoring patient activities, clinical site selection, and study design. The disclosed embodiments can provide a 90% reduction of expended human resources while maintain high quality and yield during clinical studies.

Note that while some of the embodiments discussed below are described in the context of clinical studies by contracted research organizations, this is merely one example. It will be understood that the principles of this disclosure may be implemented in any number of other suitable contexts, especially those related to collection and analysis of health data.

FIG. 1 illustrates an example network configuration 100 according to an embodiment. As shown in FIG. 1, according to embodiments of this disclosure, an electronic device 101 is included in the network configuration 100. The electronic device 101 may include at least one of a bus 110, a processor 120, a memory 130, an input/output (I/O) interface 150, a display 160, a communication interface 170, or a sensor 180. In some embodiments, the electronic device 101 may exclude at least one of the components or may add another component.

The bus 110 may include a circuit for connecting the components 120-180 with one another and transferring communications (such as control messages and/or data) between the components. The processor 120 may include one or more of a central processing unit (CPU), an application processor (AP), or a communication processor (CP). The processor 120 may perform control on at least one of the other components of the electronic device 101 and/or perform an operation or data processing relating to communication.

The memory 130 may include a volatile and/or non-volatile memory. For example, the memory 130 may store commands or data related to at least one other component of the electronic device 101. According to embodiments of this disclosure, the memory 130 may store software and/or a program 140. The program 140 may include, for example, a kernel 141, middleware 143, an application programming interface (API) 145, and/or an application program (or "application") 147. At least a portion of the kernel 141, middleware 143, or API 145 may be denoted an operating system (OS).

The kernel 141 may control or manage system resources (such as the bus 110, processor 120, or memory 130) used to perform operations or functions implemented in other programs (such as the middleware 143, API 145, or application program 147). The kernel 141 may provide an interface that allows the middleware 143, API 145, or application 147 to access the individual components of the electronic device 101 to control or manage the system resources. The middleware 143 may function as a relay to allow the API 145 or the application 147 to communicate data with the kernel 141, for example. A plurality of applications 147 may be provided. The middleware 143 may control work requests received from the applications 147, such as by allocating the priority of using the system resources of the electronic device 101 (such as the bus 110, processor 120, or memory 130) to at least one of the plurality of applications 147. The API 145 is an interface allowing the application 147 to control functions provided from the kernel 141 or the middleware 143. For example, the API 145 may include at least one interface or function (such as a command) for file control, window control, image processing, or text control.

The input/output interface 150 may serve as an interface that may, for example, transfer commands or data input from a user or other external devices to other component(s) of the electronic device 101. Further, the input/output interface 150 may output commands or data received from other component(s) of the electronic device 101 to the user or the other external devices.

The display 160 may include, for example, a liquid crystal display (LCD), a light emitting diode (LED) display, an organic light emitting diode (OLED) display, an active matrix OLED (AMOLED), a microelectromechanical systems (MEMS) display, or an electronic paper display. The display 160 can also be a depth-aware display, such as a multi-focal display. The display 160 may display various contents (such as text, images, videos, icons, or symbols) to the user. The display 160 may include a touchscreen and may receive, for example, a touch, gesture, proximity, or hovering input using an electronic pen or a body portion of the user.

The communication interface 170 may set up communication between the electronic device 101 and an external electronic device (such as a first electronic device 102, a second electronic device 104, or a server 106). For example, the communication interface 170 may be connected with a network 162 or 164 through wireless or wired communication to communicate with the external electronic device.

The electronic device 101 further includes one or more sensors 180 that can meter a physical quantity or detect an activation state of the electronic device 101 and convert metered or detected information into an electrical signal. For example, one or more sensors 180 can include one or more buttons for touch input, one or more cameras, a gesture sensor, a gyroscope or gyro sensor, an air pressure sensor, a magnetic sensor or magnetometer, an acceleration sensor or accelerometer, a grip sensor, a proximity sensor, a color sensor (such as a red green blue (RGB) sensor), a biophysical sensor, a temperature sensor, a humidity sensor, an illumination sensor, an ultraviolet (UV) sensor, an electromyography (EMG) sensor, an electroencephalogram (EEG) sensor, an electrocardiogram (ECG) sensor, an infrared (IR) sensor, an ultrasound sensor, an iris sensor, or a fingerprint sensor. The sensor(s) 180 can also include an inertial measurement unit, which can include one or more accelerometers, gyroscopes, and other components. The sensor(s) 180 can further include a control circuit for controlling at least one of the sensors included here. Any of these sensor(s) 180 can be located within the electronic device 101.

The first external electronic device 102 or the second external electronic device 104 may be a wearable device or an electronic device 101-mountable wearable device (such as a head mounted display (HMD)). When the electronic device 101 is mounted in an HMD (such as the electronic device 102), the electronic device 101 may detect the mounting in the HMD and operate in a virtual reality mode. When the electronic device 101 is mounted in the electronic device 102 (such as the HMD), the electronic device 101 may communicate with the electronic device 102 through the communication interface 170. The electronic device 101 may be directly connected with the electronic device 102 to communicate with the electronic device 102 without involving with a separate network.

The wireless communication may use at least one of, for example, long term evolution (LTE), long term evolution-advanced (LTE-A), code division multiple access (CDMA), wideband code division multiple access (WCDMA), universal mobile telecommunication system (UMTS), wireless broadband (WiBro), or global system for mobile communication (GSM), as a cellular communication protocol. The wired connection may include at least one of, for example, universal serial bus (USB), high definition multimedia interface (HDMI), recommended standard 232 (RS-232), or plain old telephone service (POTS). The network 162 may include at least one communication network, such as a computer network (like a local area network (LAN) or wide area network (WAN)), the Internet, or a telephone network.

The first and second external electronic devices 102 and 104 each may be a device of the same type or a different type from the electronic device 101. According to embodiments of this disclosure, the server 106 may include a group of one or more servers. Also, according to embodiments of this disclosure, all or some of the operations executed on the electronic device 101 may be executed on another or multiple other electronic devices (such as the electronic devices 102 and 104 or server 106). Further, according to embodiments of this disclosure, when the electronic device 101 should perform some function or service automatically or at a request, the electronic device 101, instead of executing the function or service on its own or additionally, may request another device (such as electronic devices 102 and 104 or server 106) to perform at least some functions associated therewith. The other electronic device (such as electronic devices 102 and 104 or server 106) may execute the requested functions or additional functions and transfer a result of the execution to the electronic device 101. The electronic device 101 may provide a requested function or service by processing the received result as it is or additionally. To that end, a cloud computing, distributed computing, or client-server computing technique may be used, for example.

While FIG. 1 shows that the electronic device 101 includes the communication interface 170 to communicate with the external electronic device 102 or 104 or server 106 via the network(s) 162 and 164, the electronic device 101 may be independently operated without a separate communication function, according to embodiments of this disclosure. Also, note that the electronic device 102 or 104 or the server 106 could be implemented using a bus, a processor, a memory, an I/O interface, a display, a communication interface, and an event processing module (or any suitable subset thereof) in the same or similar manner as shown for the electronic device 101.

Although FIG. 1 illustrates one example of a network configuration 100, various changes may be made to FIG. 1. For example, the network configuration 100 could include any number of each component in any suitable arrangement. In general, computing and communication systems come in a wide variety of configurations, and FIG. 1 does not limit the scope of this disclosure to any particular configuration. Also, while FIG. 1 illustrates one operational environment in which various features disclosed in this patent document can be used, these features could be used in any other suitable system.

Figure 2:
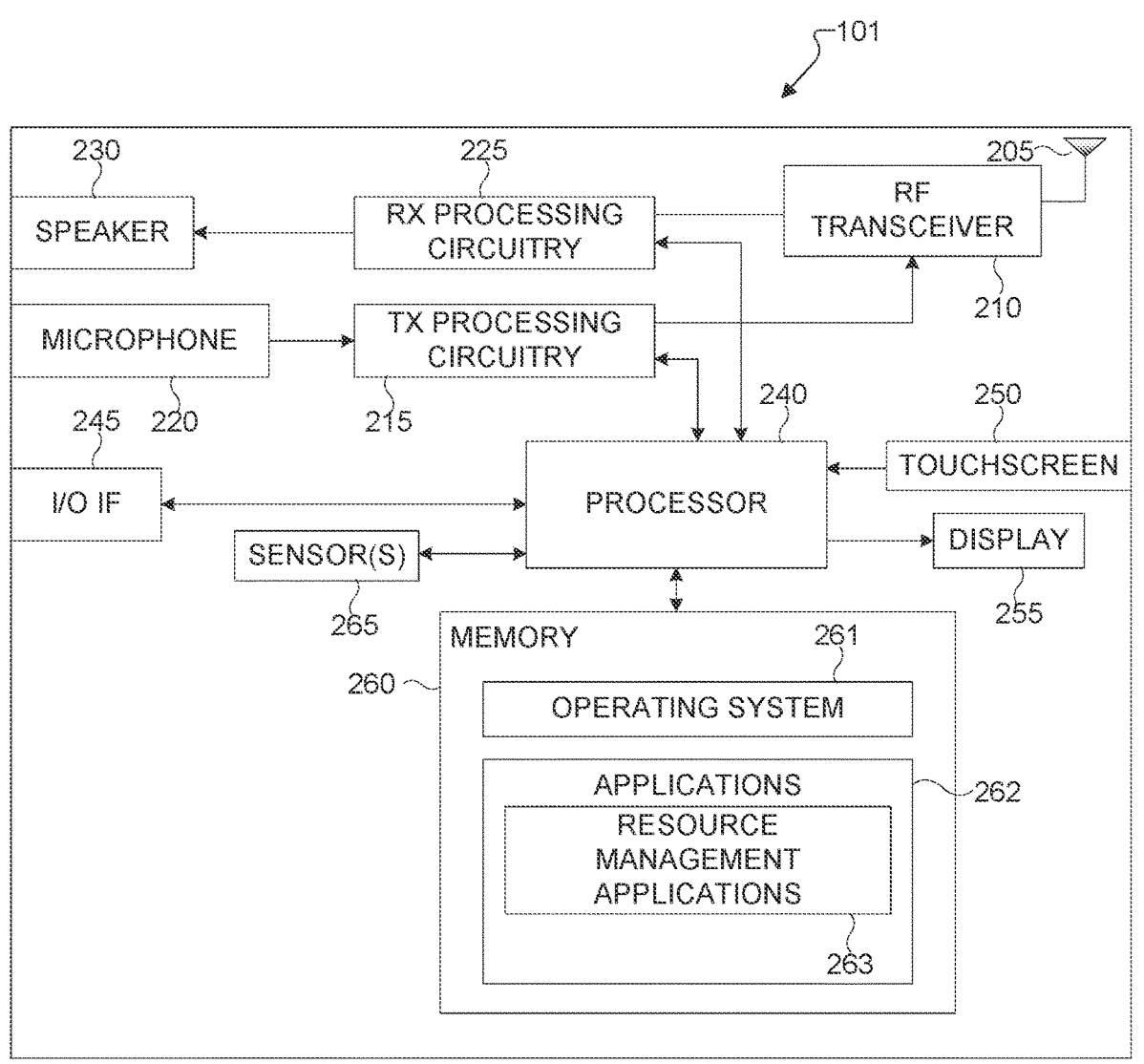
FIG. 2 illustrates an example electronic device according to an embodiment.

FIG. 2 illustrates an example electronic device 101 according to an embodiment. The electronic device 101 could represent one or more of the electronic devices 101, 102, or 104 in FIG. 1. In some embodiments, the electronic device 101 can represent a 5G capable UE. As shown in FIG. 2, the electronic device 101 includes an antenna 205, a radio frequency (RF) transceiver 210, transmit (TX) processing circuitry 215, a microphone 220, and receive (RX) processing circuitry 225. The electronic device 101 also includes a speaker 230, a processor 240, an input/output (I/O) interface (IF) 245, an input 250, a display 255, and a memory 260.

The memory 260 includes an operating system (OS) program 261 and one or more applications 262.

The RF transceiver 210 receives, from the antenna 205, an incoming RF signal transmitted by another component in a system. The RF transceiver 210 down-converts the incoming RF signal to generate an intermediate frequency (IF) or baseband signal. The IF or baseband signal is sent to the RX processing circuitry 225, which generates a processed baseband signal by filtering, decoding, and/or digitizing the baseband or IF signal. The RX processing circuitry 225 transmits the processed baseband signal to the speaker 230 (such as for voice data) or to the processor 240 for further processing.

The TX processing circuitry 215 receives analog or digital voice data from the microphone 220 or other outgoing baseband data (such as web data, e-mail, or interactive video game data) from the processor 240. The TX processing circuitry 215 encodes, multiplexes, and/or digitizes the outgoing baseband data to generate a processed baseband or If signal. The RF transceiver 210 receives the outgoing processed baseband or IF signal from the TX processing circuitry 215 and up-converts the baseband or IF signal to an RF signal that is transmitted via the antenna 205.

The processor 240 can include one or more processors or other processors and execute the OS program 261 stored in the memory 260 in order to control the overall operation of the electronic device 101. For example, the processor 240 could control the reception of forward channel signals and the transmission of reverse channel signals by the RF transceiver 210, the RX processing circuitry 225, and the TX processing circuitry 215 in accordance with well-known principles. In some embodiments, the processor 240 includes at least one microprocessor or microcontroller.

The processor 240 is also capable of executing other processes and programs resident in the memory 260. The processor 240 can move data into or out of the memory 260 as required by an executing process. In some embodiments, the processor 240 is configured to execute the applications 262 based on the OS program 261 or in response to signals received from external devices or an operator. The processor 240 can execute a resource management application 263 for monitoring system resources. The processor 240 is also coupled to the I/O interface 245, which provides the electronic device 101 with the ability to connect to other devices such as laptop computers, handheld computers and other accessories, for example, a virtual reality (VR) headset. The I/O interface 245 is the communication path between these accessories and the processor 240. The processor 240 can recognize accessories that are attached through the I/O interface 245, such as a VR headset connected to a USB port.

The processor 240 is also coupled to the input 250 and the display 255. The operator of the electronic device 101 can use the input 250 (e.g., keypad, touchscreen, button etc.) to enter data into the electronic device 101. The display 255 may be an LCD, LED, OLED, AMOLED, MEMS, electronic paper, or other display capable of rendering text and/or at least limited graphics, such as from web sites.

The memory 260 is coupled to the processor 240. Part of the memory 260 could include a random access memory (RAM), and another part of the memory 260 could include a Flash memory or other read-only memory (ROM).

The electronic device 101 further includes one or more sensors 265 that can meter a physical quantity or detect an activation state of the electronic device 101 and convert metered or detected information into an electrical signal. For example, the sensor 265 may include any of the various sensors 180 discussed above.

Although FIG. 2 illustrates one example of an electronic device 101, various changes may be made to FIG. 2. For example, various components in FIG. 2 could be combined, further subdivided, or omitted and additional components could be added according to particular needs. As a particular example, the processor 240 could be divided into multiple processors, such as one or more central processing units (CPUs) and one or more graphics processing units (GPUs). Also, while FIG. 2 illustrates the electronic device 101 configured as a mobile telephone or smart phone, electronic devices could be configured to operate as other types of mobile or stationary devices. In addition, as with computing and communication networks, electronic devices can come in a wide variety of configurations and FIG. 2 does not limit this disclosure to any particular electronic device.

Figure 3:
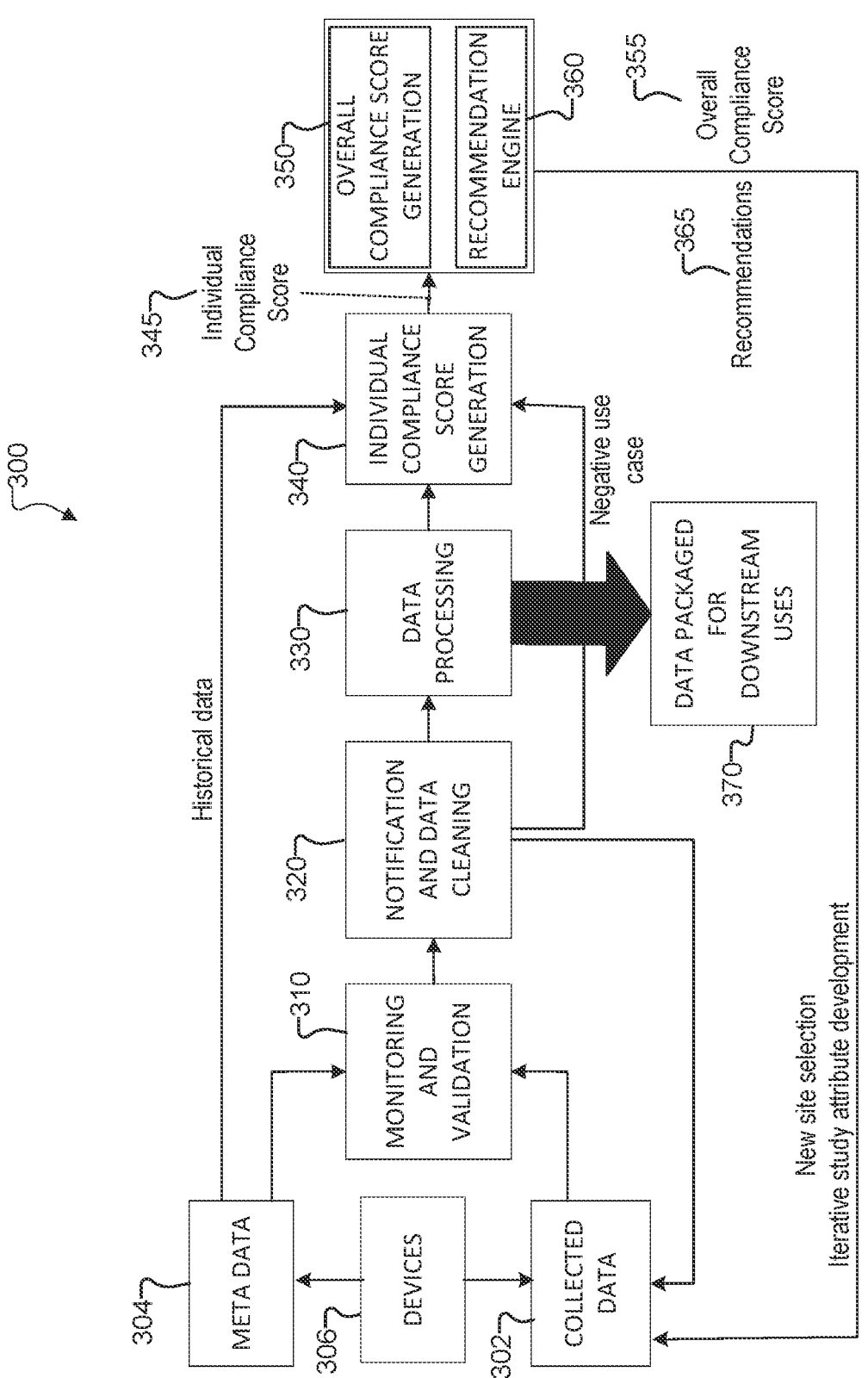
FIGS. 3 and 4 illustrate an example process for detecting issues in clinical study site and subject compliance according to an embodiment.
Figure 4:
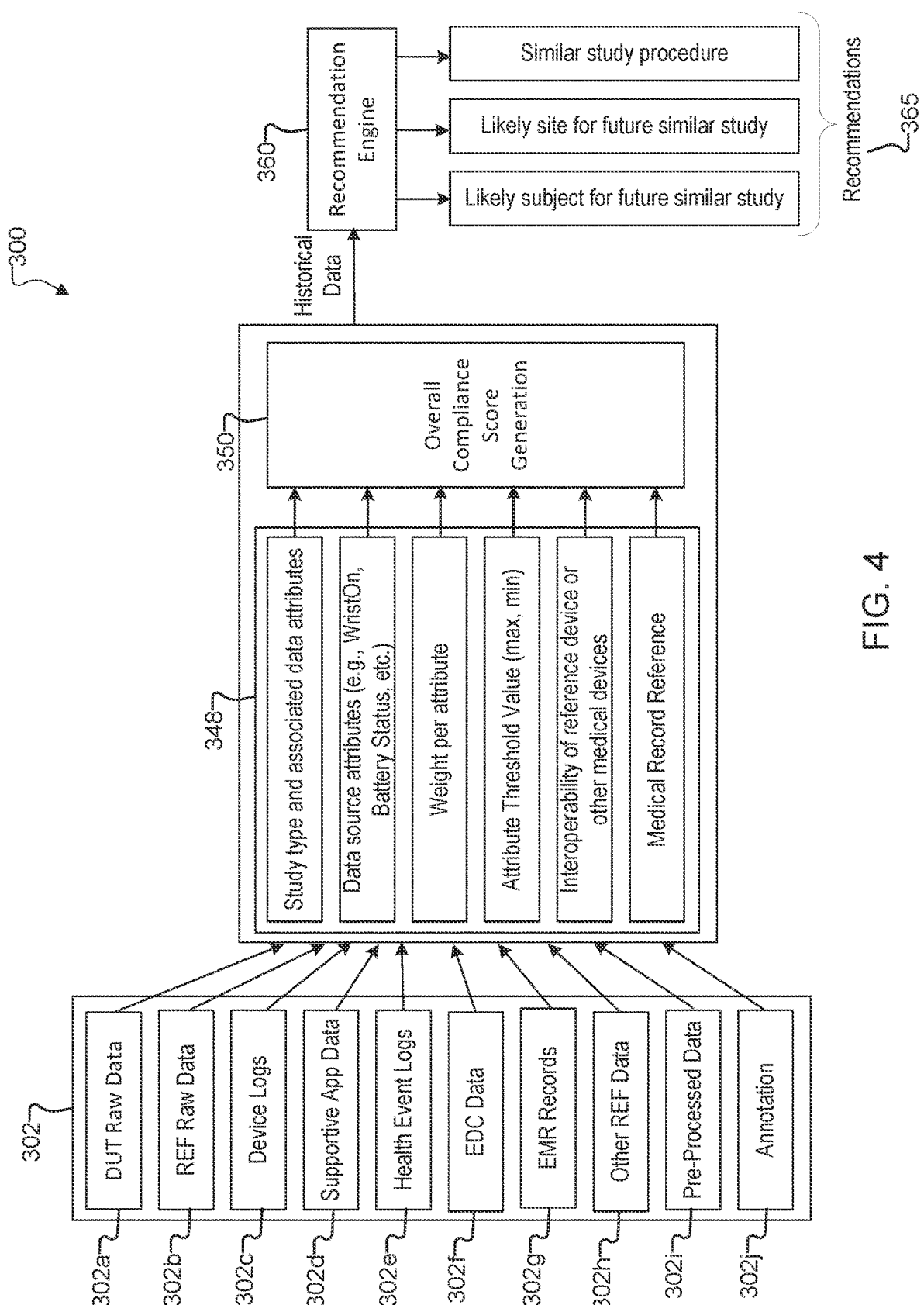

FIGS. 3 and 4 illustrates an example process 300 for detecting issues in clinical study site and subject compliance according to an embodiment. As described below, the process 300 enables detection of compliance issues using multifaceted data in real-time. Specifically, the process 300 uses data generated from a group of devices (e.g., mobile devices, wearable devices, medical devices, and the like) associated with a group of users during a clinical study. The data is evaluated and processed in real time for compliance purposes. For ease of explanation, the process 300 is described as being implemented using one or more components of the network configuration 100 described above, such as the electronic device 101. However, this is merely one example, and the process 300 could be implemented using any other suitable device(s) or component(s).

The process 300 is based on the evaluation of the interoperability of data generated from the applications running on the different devices. The data not only includes the raw signals under test (e.g., ECG, blood pressure, $SpO_2$, heart rate, etc.) for each user, but also the system event details captured during the entire journey of the clinical study. The process 300 processes the data at the individual user level, as well as the group level. For individual compliance, based on the raw data, system event data, and co-relationship data, a determination is made to confirm if the individual user should make any correction to follow the study protocol more closely, or should stay with the study for an extended time period to ensure sufficient quality data is obtained. In some embodiments, a determination can be made that the study data is not suitably detailed or reliable to continue with the study. Study staff can contact patients based on such determination(s). For the group compliance, which is based on the entire clinical site, an overall compliance score indicates the site level performance given a clinical study. For future similar clinical studies, the site may or may not be selected based on a ranking, where the overall compliance score is a significant contributor.

As shown in FIGS. 3 and 4, the electronic device 101 obtains collected data 302 and meta data 304 over a period of time during a clinical study. The collected data 302 may be obtained from one device 306 or a group of two or more devices 306 associated with each user while the user participates in the clinical study, such as a mobile phone, a wearable device, a medical device, and the like. In some embodiments, each device 306 can represent (or be represented by) one of the electronic devices 101, 102, 104 of FIG. 1. The meta data 304 may include one or more predefined configuration settings for use during run time. The collected data 302 and meta data 304 may be obtained continuously, intermittently, occasionally, according to a schedule, on demand or request, or with any other suitable frequency. That is, data collection is repeated and on-going throughout the duration of the clinical study.

The collected data 302 represents data that is generated at the devices 306 and collected directly from the devices 306. The collected data 302 can include any one or more of the following:

Device under test (DUT) raw data 302a—raw data generated by each device 306, such as measurement data.

Reference raw data 302b—reference device or reference treatment raw data, which can be used as a medical ground truth in training of machine learning systems.

Device logs 302c—these can include, for example, events, timestamps, errors, and the like, that are generated by each device 306. These can also include times that the device is worn, taken off, charged, or connected to another device.

Supportive application raw data 302d—this can include, for example, synchronization timestamps, additional measurements, and the like.

User health event logs 302e—information about the user's health or occurrence of health events. This can also include patient journals or reports created and maintained by or for one or more users during the clinical study.

Electronic data capturing (EDC) system data 302f—this can include, for example, study data, such as demographics, inclusion/exclusion of users, operational parameters, and the like.

Electronic medical records 302g—medical diagnosis, medical history, concomitant medications, clinical staff documents, and the like. In some embodiments, the records 302g are de-identified to protect privacy of the users.

Other reference data 302h from medical certified devices—this can include, for example, medical images, genomic sequence information, and the like.

Pre-processed data 302i—this can include, for example, medical image analysis, synchronous devices data, and the like.

Annotation data 302j—this can include, for example, medical over-read of ECG, polysomnography (PSG), and the like.

In other embodiments, the collected data 302 may include different or additional types of data.

The meta data 304 represents one or more predefined configuration settings for use during run time during the process 300. The meta data 304 can include any one or more of the following:

Main study attributes—attributes identifying or describing the clinical study or trial (e.g., interventional, observational, multi-center, single center, in lab, free living, multi-visit, subject demographics, measurement parameters, and the like).

Acceptance threshold—indicates minimum or maximum threshold values for the main study attributes.

History data reference—this can include, for example, prior study data, medical history information, and the like.

Interoperability level—indicates a degree of interoperability between the data generated from the applications running on the different devices 306, as discussed in greater detail below.

In other embodiments, the meta data 304 may include different or additional types of data.

As the electronic device 101 obtains the collected data 302, the electronic device 101 performs a monitoring and validation operation 310 using the collected data 302 and the meta data 304. In some embodiments, the electronic device 101 performs the monitoring and validation operation 310 continuously or regularly as the collected data 302 are received. The electronic device 101 performs the monitoring and validation operation 310 in real time to determine if there is a problem that needs to be addressed. For example, the monitoring and validation operation 310 may reveal a user inconsistency or user problem (e.g., a user wearing a monitoring device 306 incorrectly or not long enough) that needs to be addressed by promptly notifying the user.

The monitoring portion of the monitoring and validation operation 310 can include a data integrity check of the collected data 302 and meta data 304. For example, the electronic device 101 can review the collected data 302 and meta data 304 for any time gaps, data loss, time drift, and the like. The monitoring portion can also include a data completeness check of the collected data 302 and meta data 304. For example, the electronic device 101 can review the collected data 302 and meta data 304 for missing device data, partial data files, invalid pairing between the devices 306, and the like. The monitoring portion can also include study yield monitoring (e.g., monitoring for drop out subjects, screening failures, adverse events, and the like) or data yield monitoring (e.g., synchronous data sets).

The validation portion of the monitoring and validation operation 310 can include a data quality validation check of the collected data 302 and meta data 304. For example, the electronic device 101 can review the collected data 302 and meta data 304 for data accuracy (e.g., correct file types, study attributes within the expected range, correct sequence of events, and the like), data quality (e.g., signal to noise ratio within suitable range, motion artifacts, and the like), and resolution of conflicting results.

Based on the results of the monitoring and validation operation 310, the electronic device 101 performs a notification and data cleaning operation 320 using the collected data 302 and the meta data 304. In some embodiments, the electronic device 101 performs the notification and data cleaning operation 320 continuously or regularly as the collected data 302 and the meta data 304 are received. The electronic device 101 performs the notification and data cleaning operation 320 in real time to provide any notifications that are required and to "clean" (e.g., correct errors in) the collected data 302 and meta data 304 as needed, based on the results of the monitoring and validation operation 310.

In some embodiments, if the monitoring and validation operation 310 reveals that one or more users exhibit low compliance to rules during the clinical study, then during the notification and data cleaning operation 320, the electronic device 101 can contact these users to alert the users of their low compliance. Similarly, if the monitoring and validation operation 310 reveals that one or more clinical study sites exhibit low compliance to rules during the clinical study, then during the notification and data cleaning operation 320, the electronic device 101 can contact these sites to alert the sites of their low compliance. During the notification and data cleaning operation 320, the electronic device 101 can log errors (e.g., by users, sites, and the like), clean the collected data 302 and meta data 304 of the errors or generate a corrective action plan to correct the errors, and schedule follow-up interactions to determine if improvements have been made to address the errors.

The electronic device 101 also performs a data processing operation 330 using the collected data 302 and meta data 304. During the data processing operation 330, the electronic device 101 performs data re-sampling, filtering, noise removal, data alignment, data feature extraction, any other suitable algorithms, or a combination of two or more of these, in order to analyze and process the collected data 302 and meta data 304. One objective of the data processing operation 330 can be to assess performance of each device 306 or the treatment(s) under study during the clinical study. In some embodiments, during the data processing operation 330, the electronic device 101 can determine a state related to each user based on the collected data 302 and meta data 304. The state can indicate operating conditions of the group of devices 306 used by each user. For example, the state can indicate normal or abnormal operation of any of the devices 306 used by the user.

Based on the state related to the user (which indicates the operating conditions of the devices 306 used by the user), the electronic device 101 can determine an event alignment status for the devices 306. The event alignment status indicates a degree of interoperability between the devices 306 for each user. This can be particularly important when the state indicates at least one abnormal operation of the group of devices 306. To determine the event alignment status, the electronic device 101 can temporally align (e.g., align according to time of occurrence) the events that are logged by the group of devices 306 for the user. For example, the user may participate in the clinical study by using a group of devices 306 that include the user's mobile phone, a wearable device, and a certified medical device. The electronic device 101 can attempt to correlate the events of the devices 306 to identify one or more patterns of the existence of a specific event, co-existent events, or events logged in a specific sequence over a predetermined duration. It is typically important for study success that the group of devices 306 be aligned in their operation and collection of event data, which can include the collected data 302 and meta data 304. That is, there should be good correlation between data collected from different devices 306 at the same time. This can also be referred to as good interoperability between the devices 306. In some embodiments, the process 300 can achieve millisecond alignment accuracy, thus providing higher accuracy than conventional techniques.

The electronic device 101 reviews and correlates the event data in real time for compliance purposes and to detect for abnormal operations or anomalies that may negatively affect interoperability between the devices 306. For example, the electronic device 101 may determine that an event is detected by one device 306, but is not detected by another device 306 that should have detected the same event. As another example, the electronic device 101 may determine that a same event is detected by two different devices 306, but not within a threshold period of time. Such conditions are considered to be abnormal conditions or anomalies. In some embodiments, the electronic device 101 can compare the event data to a set of predefined values that indicate or represent one or more thresholds for acceptable data collection. Event data that meet or exceed the threshold values are considered to be "good" or "in compliance" or "normal operation" or otherwise indicate good interoperability between the devices 306. Alternatively, the electronic device 101 can mark or flag lower performance data sets (e.g., those that do not meet the threshold values) and generate one or more notifications for any remedies to be taken. When the electronic device 101 detects any abnormal condition, operation, or anomaly resulting from a user action or inaction (e.g., the user wearing a device 306 incorrectly or allowing a device battery to discharge), the electronic device 101 can provide a notification to the user to make a corrective action to correct the abnormal operation or anomaly in order to meet the minimum compliance requirements set forth for the clinical study.

The electronic device 101 also performs an individual compliance score generation operation 340 to determine an individual compliance score 345 for each user. The individual compliance score 345 is based on the event alignment status for the user (as determined during the data processing operation 330), and is an indication or measurement of user compliance, i.e., how well the user has complied (or is complying) with the requirements of the clinical study. To determine the individual compliance score 345 for each user, the electronic device 101 can also use historical data obtained from the meta data 304, negative use case data generated during the notification and data cleaning operation 320, any other suitable data, or a combination of these. The electronic device 101 can perform any suitable routine or algorithm to generate the individual compliance score 345 for each user. In some embodiments, if the electronic device 101 determines that the individual compliance score 345 for a user is below a predetermined threshold value, the electronic device 101 can provide at least one intervening action to the user, such as instructing the user to wear a device 306 differently or for a different period of time, charge a device 306, perform or finish a task, create a journal entry, or any other suitable action.

Using the individual compliance scores 345 for each of the users, the electronic device 101 performs an overall compliance score generation operation 350 to determine an overall compliance score 355 for the group of users in the clinical study. In some embodiments, the group of users is associated with one site for the clinical study, and the overall compliance score 355 represents a compliance score for the site. As shown in FIG. 4, in computing the overall compliance score 355, the electronic device 101 can use not only the individual compliance scores 345 for each of the users, but also use various compliance attributes 348 of the clinical study. The compliance attributes 348 can include the clinical study type, the type of all device data sources and their attributes, threshold values of the expect range (e.g., minimum and maximum) of each attribute, interoperability of each device or other medical devices, and de-identifiable subject medical records related to each user's health condition(s). Each of these compliance attributes 348 can be assigned a value, which can be stored in a memory, such as in a configuration table. In addition, each compliance attribute 348 can be assigned one or more weights, thereby resulting in weighted compliance attributes 348.

The electronic device 101 can perform any suitable routine or algorithm to generate the overall compliance score 355. For example, in some embodiments, the electronic device 101 can use machine learning techniques to generate the overall compliance score 355, the individual compliance score 345 for each user, or both. Such machine learning techniques can include presently known techniques and other techniques that may be developed in the future, including both supervised learning and unsupervised learning techniques. Some specific examples of machine learning techniques that may be suitable for use in generating the scores 345, 355 include linear regression, Naive Bayes, Random Forest, Decision Tree, logistic regression, kNN, and the like. Of course, other suitable machine learning techniques are within the scope of this disclosure.

The electronic device 101 can also perform a recommendation engine 360 to make one or more recommendations 365 related to the clinical study. For example, based on the individual compliance scores 345 for the users, the electronic device 101 can recommend a duration of the clinical study. As a particular example, if a significant subset of the users have a low individual compliance score 345, then the electronic device 101 may determine that the collected data 302 in the clinical study is flawed, and may recommend that the clinical study be ended early, or be extended for a longer period in an attempt to overcome the flawed data.

As another example, if one or more users have a high individual compliance score 345, then the electronic device 101 may recommend that these users graduate from the clinical study ahead of the schedule. Additionally or alternatively, if one or more users have a high individual compliance score 345, then the electronic device 101 may recommend that these users are good candidates for future clinical studies, since the users are likely to comply with the rules of such future clinical studies. In some embodiments, the electronic device 101 can identify a study category based on characteristics of the current clinical study, and then recommend the users with a high individual compliance score 345 for future clinical studies that belong to the same study category. In some embodiments, the electronic device 101 may also base the recommendation on a medical condition of the user. That is, the electronic device 101 may recommend a user for a future study only if the user has a medical condition that corresponds to the future study.

As yet another example, the electronic device 101 may make a recommendation for a plan modification for a future study based on the overall compliance score 355 of the current study. As a particular example, the electronic device may identify one or more factors contributing to the efficiency or accuracy of the current clinical study based on the overall compliance score 355, and then recommend the plan modification for the future study based on the factors.

In addition to generating compliance scores 345, 355 and recommendations 365, the electronic device 101 can package some or all of the collected data 302 and meta data 304 for one or more downstream uses 370. For example, the downstream uses 370 can include algorithm development, regulatory approval, and the like.

Although FIGS. 3 and 4 illustrates one example of a process 300 in which issues in clinical study site and subject compliance can be detected and related details, various changes may be made to FIGS. 3 and 4. For example, the process 300 could include any number of devices 306 in any suitable arrangement. In general, computing and communication systems come in a wide variety of configurations, and FIGS. 3 and 4 do not limit the scope of this disclosure to any particular configuration. Also, various operations in FIGS. 3 and 4 could overlap, occur in parallel, occur in a different order, or occur any number of times.

It should be noted that the various functions and operations shown and described above with respect to FIGS. 3 and 4 can be implemented in the electronic device 101 or the devices 306 in any suitable manner. For example, in some embodiments, at least some of the functions and operations can be implemented or supported using one or more software applications or other software instructions that are executed by the processor(s) 120, 240 of the electronic device 101. In other embodiments, at least some of the functions and operations can be implemented or supported using dedicated hardware components. In general, the functions and operations can be performed using any suitable hardware or any suitable combination of hardware and software/firmware instructions.

Figure 5:
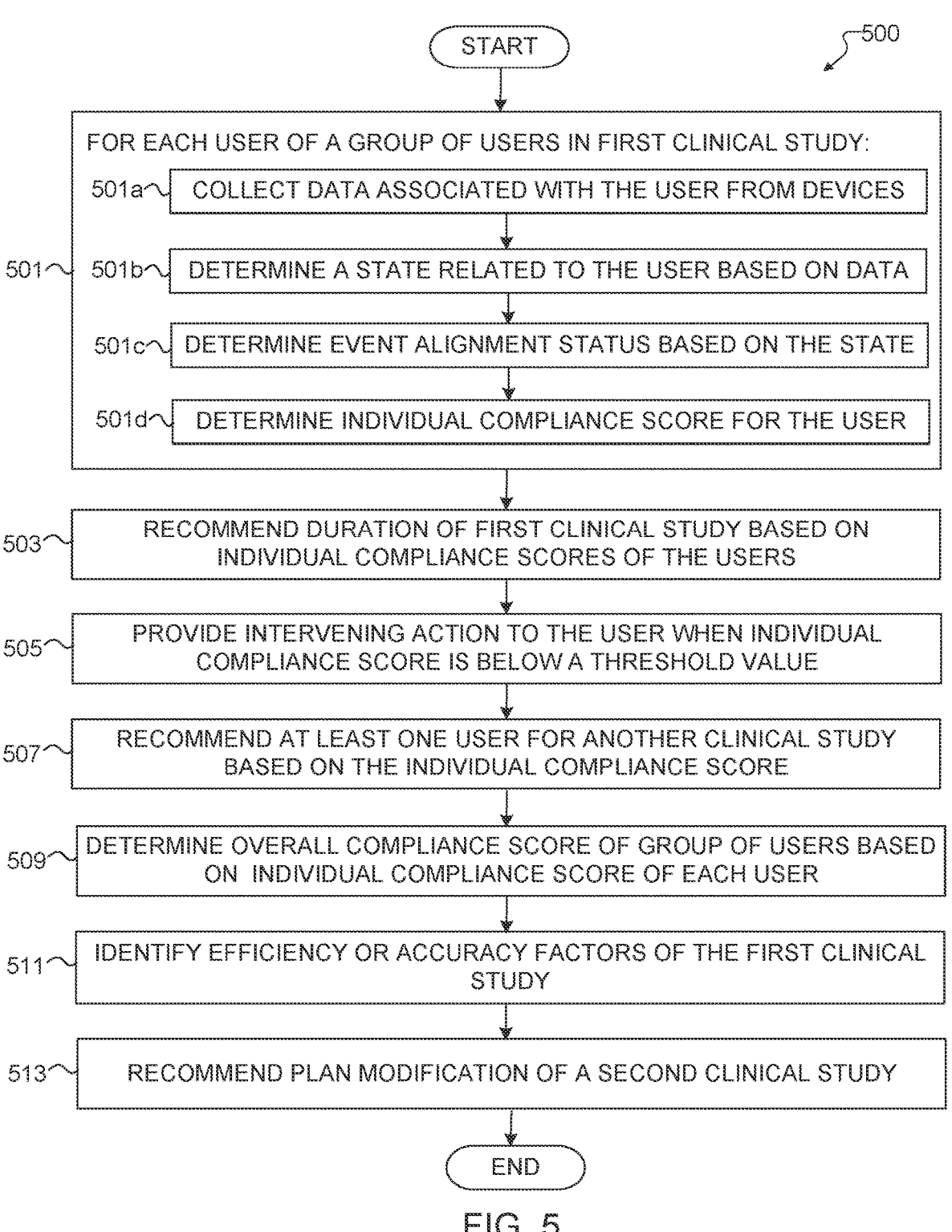
FIG. 5 illustrates an example method for detecting issues in clinical study site and subject compliance according to an embodiment.

FIG. 5 illustrates an example method 500 for detecting issues in clinical study site and subject compliance according to an embodiment. For ease of explanation, the method 500 shown in FIG. 5 is described as involving the process 300 shown in FIGS. 3 and 4. The method 500 may be performed by an electronic device, such as the electronic device 101 of FIG. 1. However, the method 500 could involve any other suitable process and be performed by any suitable device or system without departing from the scope of this disclosure.

The electronic device performs multiple operations 501 for each user of a group of users in a first clinical study. This can include, for example, the electronic device 101 performing operation 501*a*, in which the electronic device 101 collects data associated with the user, where the data includes collected data 302 and meta data 304 received from a group of devices 306 used by the user over a duration during the first clinical study. This can also include, for example, the electronic device 101 performing operation 501*b*, in which the electronic device 101 determines a state related to the user based on the data, where the state indicates operating conditions of the devices 306. This can further include, for example, the electronic device 101 performing operation 501*c*, in which the electronic device 101 determines an event alignment status by aligning events logged by the devices 306 based on the state related to the user. This can also include, for example, the electronic device 101 performing operation 501*d*, in which the electronic device 101 determines an individual compliance score 345 for the user based on the event alignment status.

At operation 503, the electronic device provides a recommended duration of the first clinical study based on the individual compliance scores of the group of users. This can include, for example, the electronic device 101 providing a recommendation 365 of the duration of the first clinical study based on the individual compliance scores 345 of the group of users.

At operation 505, the electronic device provides at least one intervening action to the user when the individual compliance score is below a predetermined threshold value. This can include, for example, the electronic device 101 instructing the user to perform a task when the user's individual compliance score 345 is below a predetermined threshold value.

At operation 507, the electronic device recommends at least one user of the group of users for another clinical study based on the individual compliance score. This can include, for example, the electronic device 101 recommending one or more users for a second clinical study that belongs to the same study category based on the individual compliance score(s) 345 of the one or more users.

At operation 509, the electronic device determines an overall compliance score of the group of users based on the individual compliance score of each user of the group of users. This can include, for example, the electronic device 101 determining the overall compliance score 355 based on the individual compliance scores 345 of the users in the group.

At operation 511, the electronic device identifies one or more factors contributing to efficiency or accuracy of the first clinical study based on the overall compliance score. This can include, for example, the electronic device 101 identifying one or more factors contributing to efficiency or accuracy of the first clinical study based on the overall compliance score 355.

At operation 513, the electronic device recommending a plan modification of a second clinical study based on the one or more factors. This can include, for example, the electronic device 101 recommending a plan modification of a future clinical study based on the one or more factors.

Although FIG. 5 illustrates one example of a method 500 for detecting issues in clinical study site and subject compliance according to an embodiment, various changes can be made to FIG. 5. For example, various steps in FIG. 5 could overlap, occur in parallel, occur serially, occur in a different order, or occur any number of times. Also, the steps of the method 500 could be implemented in any suitable manner, such as entirely within the electronic device 101 or using a combination of devices. For instance, the electronic device 101 could collect data and provide the data to a server 106, which could then process the data and generate any suitable output.

Although this disclosure has been described with reference to various example embodiments, various changes and modifications may be suggested to one skilled in the art. It is intended that this disclosure encompass such changes and modifications as fall within the scope of the appended claims.

What is claimed is:

1. A method comprising:

for each user of a group of users:

receiving, in real time via a radio frequency (RF) transceiver of an electronic device, a plurality of data associated with the user, wherein the plurality of data includes real-time raw signal data transmitted by a group of devices used by the user over a duration;

determining a state related to the user based on the plurality of data, wherein the state indicates operating conditions of the group of devices used by the user;

determining an event alignment status indicating a degree of interoperability of the group of devices by aligning events logged by the group of devices based on the state related to the user;

determining, using a machine learning system executed by at least one processor of the electronic device, an individual compliance score for the user based on the event alignment status and based on at least one of (i) historical data obtained from metadata of the plurality of data or (ii) negative use case data generated during a data cleaning operation executed by the at least one processor, wherein the machine learning system is trained via collection of raw reference device data and use of the raw reference device data as ground truths for adjusting parameters of the machine learning system; and in response to a determination that the individual compliance score is below a specified threshold value, providing at least one instruction to the user regarding a recommended use of at least one device in the group of devices;

determining, using the machine learning system, an overall compliance score of the group of users based on the individual compliance score of each user of the group of users, including:

storing one or more compliance attribute values of each user in a memory of the electronic device;

assigning one or more weights to each of the one or more compliance attribute values stored in the memory to generate one or more weighted compliance attribute values; and computing, by the machine learning system, the overall compliance score by using both the one or more weighted compliance attribute values and the individual compliance scores; and outputting, by the electronic device, a recommendation based on the individual compliance scores of the group of users or based on the overall compliance score.

2. The method of claim 1, wherein determining the event alignment status comprises:

when the state indicates at least one abnormal operation of the group of devices, correlating the events to identify one or more patterns of: existence status of a specific event, co-existent events, or events logged in a specific sequence over a predetermined duration; and determining the event alignment status based on the correlated events.

3. The method of claim 1, wherein the group of users are associated with a first clinical study, the method further comprising:

identifying a study category based on characteristics of the first clinical study; and recommending at least one user of the group of users for another clinical study that belongs to the study category based on the individual compliance score and a medical condition of the at least one user.

4. The method of claim 3, further comprising:

identifying one or more factors contributing to efficiency or accuracy of the first clinical study based on the overall compliance score; and recommending a plan modification of a second clinical study based on the one or more factors.

5. The method of claim 4, wherein the factors include (i) sources of the plurality of data, and (ii) a status of the group of devices associated with each user of the group of users.

6. An electronic device comprising:

at least one memory configured to store instructions; and at least one processor configured when executing the instructions to:

for each user of a group of users:

receive, in real time via a radio frequency (RF) transceiver of the electronic device, a plurality of data associated with the user, wherein the plurality of data includes real-time raw signal data transmitted by a group of devices used by the user over a duration;

determine a state related to the user based on the plurality of data, wherein the state indicates operating conditions of the group of devices used by the user;

determine an event alignment status indicating a degree of interoperability of the group of devices by aligning events logged by the group of devices based on the state related to the user;

determine, using a machine learning system executed by the at least one processor, an individual compliance score for the user based on the event alignment status and based on at least one of (i) historical data obtained from metadata of the plurality of data or (ii) negative use case data generated during a data cleaning operation executed by the at least one processor, wherein the machine learning system is trained via collection of raw reference device data and use of the raw reference device data as ground truths for adjusting parameters of the machine learning system; and in response to a determination that the individual compliance score is below a specified threshold value, provide at least one instruction to the user regarding a recommended use of at least one device in the group of devices;

determine, using the machine learning system, an overall compliance score of the group of users based on the individual compliance score of each user of the group of users, wherein, to determine the overall compliance score, the at least one processor is configured to:

store one or more compliance attribute values of each user in the at least one memory;

assign one or more weights to each of the one or more compliance attribute values stored in the at least one memory to generate one or more weighted compliance attribute values; and compute, by the machine learning system, the overall compliance score by using both the one or more weighted compliance attribute values and the individual compliance scores; and output a recommendation based on the individual compliance scores of the group of users or based on the overall compliance score.

7. The electronic device of claim 6, wherein, to determine the event alignment status, the at least one processor is configured to:

when the state indicates at least one abnormal operation of the group of devices, correlate the events to identify one or more patterns of: existence status of a specific event, co-existent events, or events logged in a specific sequence over a predetermined duration; and determine the event alignment status based on the correlated events.

8. The electronic device of claim 6, wherein the group of users are associated with a first clinical study, and wherein the at least one processor is further configured to:

identify a study category based on characteristics of the first clinical study; and recommend at least one user of the group of users for another clinical study that belongs to the study category based on the individual compliance score and a medical condition of the at least one user.

9. The electronic device of claim 8, wherein the at least one processor is further configured to:

identify one or more factors contributing to efficiency or accuracy of the first clinical study based on the overall compliance score; and recommend a plan modification of a second clinical study based on the one or more factors.

10. The electronic device of claim 9, wherein the factors include (i) sources of the plurality of data, and (ii) a status of the group of devices associated with each user of the group of users.

11. A non-transitory computer readable medium containing computer readable program code that, when executed, causes at least one processor of an electronic device to:

for each user of a group of users:

receive, in real time via a radio frequency (RF) transceiver of the electronic device, a plurality of data associated with the user, wherein the plurality of data includes real-time raw signal data transmitted by a group of devices used by the user over a duration;

determine a state related to the user based on the plurality of data, wherein the state indicates operating conditions of the group of devices used by the user;

determine an event alignment status indicating a degree of interoperability of the group of devices by aligning events logged by the group of devices based on the state related to the user;

determine, using a machine learning system executed by the at least one processor, an individual compliance score for the user based on the event alignment status and based on at least one of (i) historical data obtained from metadata of the plurality of data or (ii) negative use case data generated during a data cleaning operation executed by the at least one processor, wherein the machine learning system is trained via collection of raw reference device data and use of the raw reference device data as ground truths for adjusting parameters of the machine learning system; and in response to a determination that the individual compliance score is below a specified threshold value, provide at least one instruction to the user regarding a recommended use of at least one device in the group of devices;

determine, using the machine learning system, an overall compliance score of the group of users based on the individual compliance score of each user of the group of users, wherein the computer readable program code that when executed causes the at least one processor to determine the overall compliance score comprises computer readable program code that when executed causes the at least one processor to:

store one or more compliance attribute values of each user in a memory of the electronic device;

assign one or more weights to each of the one or more compliance attribute values stored in the memory to generate one or more weighted compliance attribute values; and compute, by the machine learning system, the overall compliance score by using both the one or more weighted compliance attribute values and the individual compliance scores; and output a recommendation based on the individual compliance scores of the group of users or based on the overall compliance score.

12. The non-transitory computer readable medium of claim 11, wherein the computer readable program code that when executed causes the at least one processor to determine the event alignment status comprises computer readable program code that when executed causes the at least one processor to:

when the state indicates at least one abnormal operation of the group of devices, correlate the events to identify one or more patterns of: existence status of a specific event, co-existent events, or events logged in a specific sequence over a predetermined duration; and determine the event alignment status based on the correlated events.

13. The non-transitory computer readable medium of claim 11, wherein the group of users are associated with a first clinical study, and wherein the computer readable program code, when executed, further causes the at least one processor to:

identify a study category based on characteristics of the first clinical study; and recommend at least one user of the group of users for another clinical study that belongs to the study category based on the individual compliance score and a medical condition of the at least one user.

14. The non-transitory computer readable medium of claim 13, wherein the computer readable program code, when executed, further causes the at least one processor to:

identify one or more factors contributing to efficiency or accuracy of the first clinical study based on the overall compliance score; and recommend a plan modification of a second clinical study based on the one or more factors.

15. The non-transitory computer readable medium of claim 14, wherein the factors include (i) sources of the plurality of data, and (ii) a status of the group of devices associated with each user of the group of users.

16. The method of claim 1, wherein, to determine at least one of the individual compliance scores or the overall compliance score, the machine learning system performs at least one of a linear regression technique, a Naive Bayes technique, a Random Forest technique, a Decision Tree technique, a logistic regression technique, or a k-nearest neighbors (kNN) technique.

17. The method of claim 1, wherein the one or more compliance attribute values are associated with one or more compliance attributes comprising at least one of:

device types of the group of devices;

at least one acceptance threshold value associated with an expected value range; or the degree of interoperability of the group of devices.

18. The electronic device of claim 6, wherein, to determine at least one of the individual compliance scores or the overall compliance score, the machine learning system is configured to perform at least one of a linear regression technique, a Naive Bayes technique, a Random Forest technique, a Decision Tree technique, a logistic regression technique, or a k-nearest neighbors (kNN) technique.

19. The electronic device of claim 6, wherein the one or more compliance attribute values are associated with one or more compliance attributes comprising at least one of:

device types of the group of devices;

at least one acceptance threshold value associated with an expected value range; or the degree of interoperability of the group of devices.

20. The non-transitory computer readable medium of claim 11, wherein, to determine at least one of the individual compliance scores or the overall compliance score, the machine learning system is configured to perform at least one of a linear regression technique, a Naive Bayes technique, a Random Forest technique, a Decision Tree technique, a logistic regression technique, or a k-nearest neighbors (kNN) technique.

21. The non-transitory computer readable medium of claim 11, wherein the one or more compliance attribute values are associated with one or more compliance attributes comprising at least one of:

device types of the group of devices;

at least one acceptance threshold value associated with an expected value range; or the degree of interoperability of the group of devices.

\* \* \* \* \*